(12) United States Patent
Stessman et al.

(10) Patent No.: US 8,958,877 B2
(45) Date of Patent: Feb. 17, 2015

(54) IMPLANTABLE DEVICE WITH BIAS FOR MRI

(71) Applicant: Cardiac Pacemakers, Inc., St. Paul, MN (US)

(72) Inventors: Nicholas J. Stessman, Minneapolis, MN (US); Michael J. Lyden, Shoreview, MN (US); Thomas M. Bocek, Seattle, WA (US); William J. Linder, Golden Valley, MN (US); Joseph M. Bocek, Seattle, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/301,002

(22) Filed: Jun. 10, 2014

(65) Prior Publication Data

US 2014/0296699 A1    Oct. 2, 2014

Related U.S. Application Data

(63) Continuation of application No. 12/976,862, filed on Dec. 22, 2010, now Pat. No. 8,755,886.

(60) Provisional application No. 61/291,438, filed on Dec. 31, 2009.

(51) Int. Cl.
    *A61N 1/00*    (2006.01)
    *A61B 5/05*    (2006.01)
    *A61N 1/08*    (2006.01)

(52) U.S. Cl.
    CPC .............. *A61N 1/08* (2013.01); *A61N 2001/086* (2013.01)
    USPC .......................................................... 607/34

(58) Field of Classification Search
    USPC ....................................... 607/28, 34; 600/422
    See application file for complete search history.

(56) References Cited

U.S. PATENT DOCUMENTS

| | | | |
|---|---|---|---|
| 6,795,730 | B2 | 9/2004 | Connelly et al. |
| 6,925,328 | B2 | 8/2005 | Foster et al. |
| 7,369,898 | B1 | 5/2008 | Kroll et al. |
| 7,742,825 | B2 | 6/2010 | Gray et al. |
| 8,755,886 | B2 | 6/2014 | Stessman et al. |
| 2002/0169374 | A1 | 11/2002 | Jevtic |
| 2008/0221638 | A1 | 9/2008 | Wedan et al. |
| 2009/0149905 | A1 | 6/2009 | Lyden et al. |
| 2011/0160803 | A1 | 6/2011 | Stessman et al. |

OTHER PUBLICATIONS

"U.S. Appl. No. 12/976,862, Final Office Action mailed Dec. 20, 2013", 8 pgs.
"U.S. Appl. No. 12/976,862, Non Final Office Action mailed Aug. 23, 2013", 6 pgs.
"U.S. Appl. No. 12/976,862, Notice of Allowance mailed Feb. 11, 2014", 7 pgs.

(Continued)

*Primary Examiner* — Nicole F Lavert
(74) *Attorney, Agent, or Firm* — Schwegman, Lundberg & Woessner, P.A.

(57) ABSTRACT

An ambulatory or implantable device, such as a pacer, defibrillator, or other cardiac rhythm management device, can tolerate magnetic resonance imaging (MRI) or other noise without turning on an integrated circuit diode by selectively providing a bias voltage that can overcome an expected induced voltage resulting from the MRI or other noise.

20 Claims, 9 Drawing Sheets

(56) References Cited

OTHER PUBLICATIONS

"U.S. Appl. No. 12/976,862, Response filed Jan. 23, 2014 to Final Office Action mailed Dec. 20, 2013", 9 pgs.
"U.S. Appl. No. 12/976,862, Response filed Aug. 1, 2013 to Restriction Requirement mailed Jul. 1, 2013", 8 pgs.
"U.S. Appl. No. 12/976,862, Response filed Nov. 6, 2013 to Non Final Office Action mailed Aug. 23, 2013", 10 pgs.
"U.S. Appl. No. 12/976,862, Restriction Requirement mailed Jul. 1, 2013", 7 pgs.

IMPLANTABLE DEVICE WITH BIAS FOR MRI

CLAIM OF PRIORITY

This application is a continuation of U.S. patent application Ser. No. 12/976,862, filed on Dec. 22, 2010, which claims the benefit of priority under 35 U.S.C. §119(e) of U.S. Provisional Patent Application Ser. No. 61/291,438, filed on Dec. 31, 2009, each of which is herein incorporated by reference in its entirety.

BACKGROUND

Implantable medical devices (IMDs) can perform a variety of diagnostic or therapeutic functions. For example, an IMD can include one or more cardiac function management features, such as to monitor the heart or to provide electrical stimulation to a heart or to the nervous system, such as to diagnose or treat a subject, such as one or more electrical or mechanical abnormalities of the heart. Examples of IMDs can include pacers, automatic implantable cardioverter-defibrillators (ICDs), or cardiac resynchronization therapy (CRT) devices, neural stimulation devices, among others.

Nuclear magnetic resonance imaging (MRI), is a medical imaging technique that can be used to visualize internal structure of the body. MRI is an increasingly common diagnostic tool, but can pose risks to a person with an IMD, such as a patient undergoing an MRI scan or a person nearby MRI equipment, or to people having a conductive implant.

In a MR field, an item, such as an IMD, can be referred to as "MR Safe" if the item poses no known hazard in all MRI environments. In an example, MR Safe items can include non-conducting, non-metallic, non-magnetic items, such as a glass, porcelain, a non-conductive polymer, etc. An item can be referred to as "MR Conditional" in the MR field if the item has been demonstrated to pose no known hazards in a specified MRI environment with specified conditions of use (e.g., static magnetic field strength, spatial gradient, time-varying magnetic fields, RF fields, etc.). In certain examples, MR Conditional items can be labeled with testing results sufficient to characterize item behavior in a specified MRI environment. Testing can include, among other things, magnetically induced displacement force or torque, heating, induced current or voltage, or one or more other factors. An item known to pose hazards in all MRI environments, such as a ferromagnetic scissors, can be referred to as "MR Unsafe."

Overview

The present inventors have recognized, among other things, that IMDs can include or be coupled to long conductors, such as a leadwire carrying one or more distal electrostimulation or sensing electrodes contacting a desired tissue region of the patient. This can potentially be susceptible to developing a significant MRI gradient induced electromagnetic field (EMF), such as along electrodes located at a distal end of the leadwires and at the IMD case housing its electronics. MRI gradient induced EMF can also exist between significantly separated electrodes. Leadwires and other such elongated conductors included in or coupled to an IMD can also act as antenna, and can therefore also be susceptible to RF emissions from the MRI machine.

Some illustrative examples of IMDs that can include or be coupled to elongated electrical connections to the patient can include, but are not limited to, the following: (1) neuromodulators, such as deep brain stimulators (DBS), various pain control devices, or systems that can stimulate the spinal cord, muscle tissue, or other nerves of the body, e.g., a vagal nerve stimulator (VNS); (2) cardiac pacers; (3) automatic implantable cardioverter defibrillators (AICDs); (3) implantable diagnostic devices such as to monitor cardiac function, e.g., a loop recorder/Holter-monitor-like recording device; or (4) cochlear implants. The present subject matter, such as described in detail herein, can be applied to these and other ambulatory medical devices or IMDs.

This document describes systems, devices, and methods that can include an ambulatory or implantable device, such as a pacer, defibrillator, or other cardiac rhythm management device, can tolerate magnetic resonance imaging (MRI) or other noise without turning on an integrated circuit diode by selectively providing a bias voltage that can overcome an expected induced voltage resulting from the MRI or other noise.

Example 1 includes subject matter that can use or comprise an apparatus that can comprise an implantable medical device. In this example, the implantable medical device can comprise an electrical energy delivery circuit. In this example, the electrical energy delivery circuit can comprise: an integrated circuit including a diode having first and second terminals, wherein a first terminal of the diode is electrically coupled to a first reference voltage; and energy output circuitry referenced to a second reference voltage that is set at a specified value that is configured to avoid turn-on of the diode during at least one of: a magnetic resonance imaging (MRI) scanning, of a subject in which the implantable medical device is implanted, in an MRI scanner; an electrocautery of the subject; or a radiofrequency (RF) ablation of the subject.

In Example 2, the subject matter of Example 1 can optionally be configured such that the energy output circuitry is referenced to a second reference voltage that is set at a specified value that avoids turn-on of the diode during at least a magnetic resonance imaging (MRI) scanning, of a subject in which the implantable medical device is implanted, in an MRI scanner.

In Example 3, the subject matter of any one of Examples 1-2 can optionally be configured such that the energy output circuitry is referenced to the first reference voltage during a first mode of operation of the implantable medical device and referenced to a second reference voltage during a second mode of operation, and comprising: a controller circuit, configured to selectively connect the energy output circuitry to the first reference voltage during the first mode of operation, and to the second reference voltage during the second mode of operation, wherein the second mode of operation is configured to inhibit turn-on of the diode in the presence of noise interference.

In Example 4, the subject matter of any one of Examples 1-3 can optionally be configured such that the energy output circuitry comprises a recharge switch that is closed during a recharge pulse delivered in response to completion of delivery of an electrostimulation pulse, wherein the recharge switch is referenced to the first reference voltage during a first mode of operation of the implantable medical device and referenced to a second reference voltage during a second mode of operation.

In Example 5, the subject matter of any one of Examples 1-4 can optionally be configured such that the energy output circuitry comprises an electrostimulation supply capacitor, wherein the electrostimulation supply capacitor is referenced to the first reference voltage during a first mode of operation of the implantable medical device and referenced to a second reference voltage during a second mode of operation.

In Example 6, the subject matter of any one of Examples 1-5 can optionally be configured such that the energy output circuitry comprises a coupling capacitor, wherein the coupling capacitor is referenced to the first reference voltage during a first mode of operation of the implantable medical device and referenced to a second reference voltage during a second mode of operation.

In Example 7, the subject matter of any one of Examples 1-6 can optionally comprise an electrostimulation switch, configured to deliver energy from the electrostimulation supply capacitor during the electrostimulation pulse, and wherein the recharge switch is configured to alter charge on the coupling capacitor during the recharge pulse.

In Example 8, the subject matter of any one of Examples 1-7 can optionally be configured such that the electrostimulation switch and the recharge switch are located on the integrated circuit with the diode.

In Example 9, the subject matter of any one of Examples 1-8 can optionally be configured such that the second reference voltage is set at a specified value that avoids turn-on of the diode during a magnetic resonance imaging (MRI) scanning in an MRI scanner.

In Example 10, the subject matter of any one of Examples 1-9 can optionally be configured such that the first reference voltage is set to a more negative voltage than the second reference voltage.

In Example 11, the subject matter of any one of Examples 1-10 can optionally be configured such that the first reference voltage is set to a negative battery terminal voltage.

In Example 12, the subject matter of any one of Examples 1-10 can optionally be configured such that the second reference voltage is set to a negative battery terminal voltage.

Example 13 can include or use, or can be combined with the subject matter of any one of Examples 1-12 to include or use subject matter that can comprise an apparatus. In this example, the apparatus can comprise an implantable medical device. In this example, the implantable medical device can comprise an electrical energy delivery circuit, comprising: an integrated circuit including a diode having first and second terminals, wherein a first terminal of the diode is coupled (e.g., electrically connected) to a first reference voltage; and energy output circuitry referenced to the first reference voltage during a first mode of operation of the implantable medical device and referenced to a second reference voltage during a second mode of operation, wherein the second reference voltage is set at a specified value that avoids turn-on of the diode during a magnetic resonance imaging (MRI) scanning in an MRI scanner. In this example, the energy output circuitry can comprise: an electrostimulation supply capacitor, configured to store an electrostimulation voltage to be delivered to a subject; an electrostimulation switch, configured to selectively conduct current from the electrostimulation supply capacitor to be provided to the subject, wherein the electrostimulation switch is located on the integrated circuit with the diode; a coupling capacitor, configured to be located in the electrostimulation current path during an electrostimulation pulse, and configured to be discharged during a recharge pulse; and a recharge switch, configured to selectively discharge the coupling capacitor during the recharge pulse, wherein the recharge switch is located on the integrated circuit with the diode; and a controller circuit, configured to selectively connect the energy output circuitry to the first reference voltage during the first mode of operation, and to the second reference voltage during the second mode of operation, wherein the second mode of operation is configured to provide increased noise-immunity to the implantable medical device by inhibiting turn-on of the diode in the presence of noise interference.

In Example 14, the subject matter of any one of Examples 1-13 can optionally be configured to selectively connect the recharge switch to the second reference voltage during the second mode of operation.

In Example 15, the subject matter of any one of Examples 1-14 can optionally be configured to additionally connect the electrostimulation supply capacitor to the second reference voltage during the second mode of operation.

Example 16 can include or use subject matter, or can be combined with the subject matter of any one of Examples 1-15 to include or use subject matter comprising: providing an implantable medical device comprising a first mode, configured for operation in an environment that does not include magnetic resonance imaging (MRI) scanning, electrocautery, or radiofrequency (RF) ablation of a subject in which the implantable medical device is implanted, and comprising a second mode configured for operation in an environment that does include at least one of resonance imaging (MRI) scanning, electrocautery, or radiofrequency (RF) ablation of a subject in which the implantable medical device is implanted; and referencing energy output circuitry of the implantable medical device to a first reference voltage during the first mode and to a second reference voltage during the second mode.

In Example 17, the subject matter of any one of Examples 1-16 can optionally be configured or performed such that the referencing comprises referencing the energy output circuitry to a second reference voltage that is set to avoid turn-on of an integrated circuit diode in the implantable medical device during at least one of: a magnetic resonance imaging (MRI) scanning, of a subject in which the implantable medical device is implanted, in an MRI scanner; an electrocautery of the subject; or a radiofrequency (RF) ablation of the subject.

In Example 18, the subject matter of any one of Examples 1-17 can optionally be configured or performed such that the referencing comprises referencing the energy output circuitry to a second reference voltage that is set to avoid turn-on of an integrated circuit diode in the implantable medical device during a magnetic resonance imaging (MRI) scanning, of a subject in which the implantable medical device is implanted, in an MRI scanner.

In Example 19, the subject matter of any one of Examples 1-18 can optionally be configured or performed such that the referencing comprises referencing an electrostimulation recharge switch to the first reference voltage during the first mode and to the second reference voltage during the second mode.

In Example 20, the subject matter of any one of Examples 1-19 can optionally be configured or performed such that the referencing comprises referencing an electrostimulation supply capacitor to the first reference voltage during the first mode and to the second reference voltage during the second mode.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
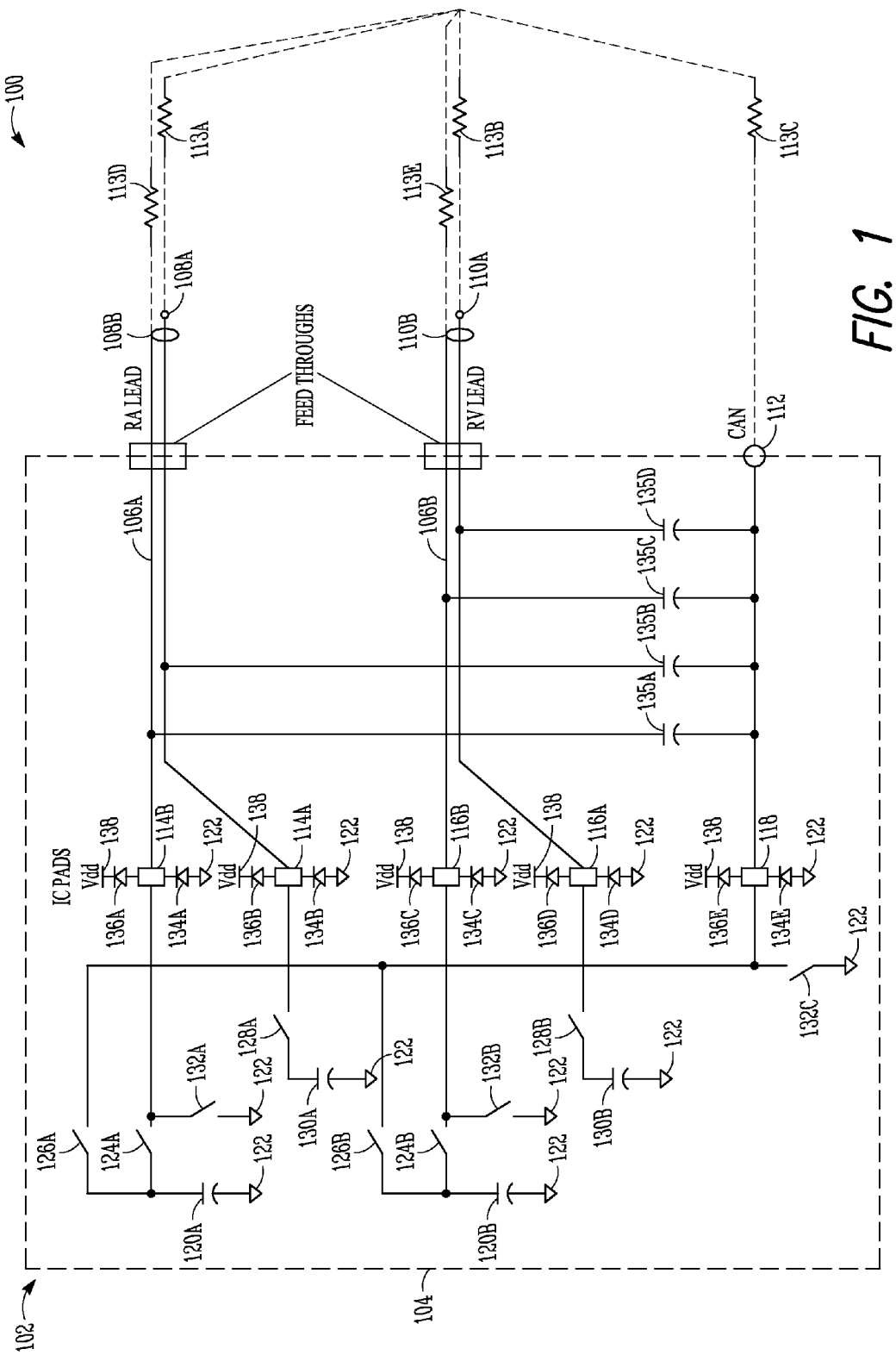
FIG. 1 illustrates an example of portions of a system that can include an implantable medical device (IMD) or other ambulatory medical device, such as cardiac function management device.

Nuclear magnetic resonance (NMR) devices (e.g., an MRI scanner, an NMR spectrometer, or other NMR device) can produce both static and time-varying magnetic fields. For example, an MRI scanner can provide a strong static magnetic field, $B_0$, such as to align nuclei within a subject to the axis of the $B_0$ field. The $B_0$ can provide a slight net magnetization (e.g., a "spin polarization") among the nuclei in bulk because the spin states of the nuclei are not randomly distributed among the possible spin states. Because the resolution attainable by NMR devices can be related to the magnitude of the $B_0$ field, a stronger $B_0$ field can be used to spin polarize the subject's nuclei to obtain finer resolution images. NMR devices can be classified according the magnitude of the $B_0$ field used during imaging, such as a 1.5 Tesla $B_0$ field, a 3.0 Tesla $B_0$ field, etc.

After nuclei are aligned using the $B_0$ field, one or more radio frequency (RF) magnetic excitation pulses can be delivered such as to alter the alignment of specified nuclei (e.g., within a particular volume or plane to be imaged within the subject). The power, phase, and range of frequencies of the one or more RF excitation pulses can be selected, such as depending on the magnitude of the $B_0$ field, the type or resonant frequency of the nuclei to be imaged, or one or more other factors. After the RF excitation pulses are turned off, one or more RF receivers can be used to detect a time-varying magnetic field (e.g., a flux) developed by the nuclei as they relax back to a lower energy state, such as the spin polarized state induced by the static magnetic field, $B_0$.

One or more gradient magnetic fields can also be provided during MR, such as to create a slight position-dependent variation in the static polarization field. The variation in the static polarization field slightly alters the resonant frequency of the relaxing nuclei, such as during relaxation after excitation by the one or more RF pulses. Using the gradient field along with the static field can provide "spatial localization" of signals detected by the RF receiver, such as by using frequency discrimination. Using a gradient field allows a volume or plane to be imaged more efficiently. In a gradient field example, signals received from relaxing nuclei can include energy in respective unique frequency ranges corresponding to the respective locations of the nuclei.

Active MRI equipment can induce unwanted torques, forces, or heating in an IMD or other conductive implant, or can interfere with operation of the IMD. In certain examples, the interference can include disruption in sensing by the IMD, interference in communication between the IMD and other implants or external modules during MRI operation, or disruption in monitoring or therapeutic function of the IMD.

During an MRI scan, the one or more RF excitation pulses can include energy delivered at frequencies from less than 10 MHz to more than 100 MHz, such as corresponding to the nuclear magnetic resonances of the subject nuclei to be imaged. The gradient magnetic field can include energy delivered at frequencies lower than the RF excitation pulses, because most of the AC energy included in the gradient field is provided when the gradient field is ramping or "slewing." The one or more gradient magnetic fields can be provided in multiple axes, such as including individual time-varying gradient fields provided in each of the axes to provide imaging in multiple dimensions.

In an example, the static field, $B_0$, can induce unwanted forces or torques on ferromagnetic materials, such as steel or nickel. The forces or torques can occur even when the materials are not directly within the "bore" of the MRI equipment-because significant fields can exist near the MRI equipment. Moreover, if an electric current is switched on or off in the presence of the $B_0$ field, a significant torque or force can be suddenly imposed in the plane of the circulation of the current, even though the $B_0$ field itself is static. The induced force or torque can be minimal for small currents, but the torque can be significant for larger currents, such as those delivered during defibrillation shock therapy. For example, assuming the circulating current is circulating in a plane normal (e.g., perpendicular) to the static field, the torque can be proportional to the magnitude of the $B_0$ field, multiplied by the surface area of the current loop, multiplied by the current.

Time-varying fields, such as the gradient field or the field associated with the RF excitation pulse, can present different risks than the static field, $B_0$. For example, the behavior of a wire loop in the presence of a time-varying magnetic field can be described using Faraday's law, which can be represented by $$\varepsilon = -\frac{d\Phi_{B_1}}{dt},$$

in which $\varepsilon$ can represent the electromotive force (e.g., in volts), such as developed by a time-varying magnetic flux. The magnetic flux can be represented as $$\Phi_{B1} = \iint_S \hat{A}_1 \times dS,$$

in which $B_1$ can represent an instantaneous magnetic flux density vector (e.g., in Webers per square meter, or Tesla). If $B_1$ is relatively uniform over the surface S, then the magnetic flux can be approximately $\Phi_{B1}=\|B_1\|\|A\|$, where A can represent the area of the surface S. Operating MRI equipment can produce a time-varying gradient field having a slew rates in excess of 100 Tesla per second (T/s). The slew rate is the "slope" of the gradient field, $$\frac{d\Phi_{B1}}{dt}.$$

The electromotive force (EMF) of Faraday's law can cause an unwanted heating effect in a conductor—regardless of whether the conductor is ferromagnetic. EMF can induce current flow in a conductor (e.g., a housing of an IMD, one or more other conductive regions within an IMD, or one or more other conductive implants). The induced current can dissipate energy and can oppose the direction of the change of the externally applied field (e.g., given by Lenz's law). The induced current tends to curl away from its initial direction, forming an "eddy current" over the surface of the conductor, such as due to Lorentz forces acting upon electrons moving through the conductor. Because non-ideal conductors have a finite resistivity, the flow of induced current through the conductor can dissipate heat. The induced heat can cause a significant temperature rise in or near the conductor over the duration of the scan. The power dissipated by the eddy current can be proportional to the square of both the peak flux density and the frequency of the excitation.

Generally, induced currents, such as induced by the RF magnetic excitation pulse, can concentrate near the surface of a conductor, a phenomenon that can be referred to as the skin effect. The skin effect can limit both the magnitude and depth of the induced current, thus reducing power dissipation. However, the gradient field can include energy at a much lower frequency than the RF magnetic excitation field, which can more easily penetrate through the housing of the IMD. Unlike the field from the RF excitation pulse, the gradient field can more easily induce bulk eddy currents in one or more conductors within the IMD housing, such as within one or more circuits, capacitors, batteries, or other conductors.

Aside from heating, the EMF can create, among other things, non-physiologic voltages that can cause erroneous sensing of cardiac electrical activity, or the EMF can create a voltage sufficient to depolarize cardiac tissue or render the cardiac tissue refractory, possibly affecting pacing therapy. In an illustrative example, an IMD can be connected to one or more leads, such as one or more subcutaneous or intravascular leads positioned to monitor the patient, or to provide one or more therapies to the patient. In this illustrative example, a surface area of a "circuit" including the lead, the housing of the IMD, and a path through at least partially conductive body tissue between an electrode on the lead and the IMD housing can be more than 300 square centimeters, or more than 0.03 square meters. Thus, using Faraday's law, the electromotive force (EMF) developed through the body tissue between the electrode (e.g., a distal tip or ring electrode) of the lead and the housing of the IMD can be more than 0.03 square meters times 100 t/s, or more than 3 volts.

This document describes, among other things, systems, devices and methods that can include an ambulatory or implantable device, such as a pacer, defibrillator, or other cardiac rhythm management device, can tolerate magnetic resonance imaging (MRI) or other noise without turning on an integrated circuit diode by selectively providing a bias voltage that can overcome an expected induced voltage resulting from the MRI or other noise.

FIG. 1 illustrates an example of portions of a system 100 that can include an implantable medical device (IMD) 102 or other ambulatory medical device, such as cardiac function management device, such as can be configured to move about with the associated subject, such as during chronic activities of daily living. In an example, as explained in more detail below, the IMD 102 can include a pacer, such as for treating bradyarrythmia, with its electrostimulation output circuit contained within an IMD case or housing of an IMD electronics unit 104, which can customarily be implanted in a pectoral region of a patient. In an example, in addition to the IMD 102, the system 100 can include implantable right atrial and right ventricular pacing leads, which can be customarily routed transvenously to the patient's heart. The system 100 can also include other implantable leads, such as a coronary sinus (CS) lead, which can provide one or more electrodes in association with the left atrium or left ventricle.

In an example, the IMD 102 can include an IMD electronics unit 104. The IMD electronics unit 104 can be coupled to one or more electrodes, such as by one or more implantable leads 106 that can be connected to the electronics unit 104. In an example, such leads can include a right atrial (RA) lead 106A and a right ventricular (RV) lead 106B. In an example, the electronics unit 104 can be coupled to one or more electrodes located in association with a left atrium or left ventricle, such as by using a lead that can be introduced into the coronary vasculature, such as via the coronary sinus and great cardiac vein. In an example, the RA lead 106A can include one or more electrodes, such as a RA distal tip electrode 108A and a slightly more proximal RA ring electrode 108B. In an example, the RV lead 106B can include one or more electrodes, such as a RV distal tip electrode 110A and a slightly more proximal RA ring electrode 110B. The IMD electronics unit 104 can include one or more electrodes, such as a can electrode 112 located on a conductive portion of a housing hermetically enclosing the electronics, or a header electrode located on an insulating header extending from the housing. In an example, the IMD electronics unit 104 can also include a communication circuit, such as to communicate with an external local interface device or an external remote interface device, which can also be part of the system 100.

In the example of FIG. 1, the resistors 113A, 113B, and 113C can represent tissue impedances. For example, the impedance between the RA electrode 108A and the RV electrode 110A can be represented by the sum of the tissue resistances of the resistors 113A and 113B; the impedance between the RA electrode 108B and the RV electrode 110B can be represented by the sum of the tissue resistances of the resistors 113D and 113E; the impedance between the RA electrode 108B and the RV electrode 110A can be represented by the sum of the tissue resistances of the resistors 113D and 113B; the impedance between the RA electrode 108A and the RV electrode 110B can be represented by the sum of the tissue resistances of the resistors 113A and 113E; the impedance between the respective RA electrodes 108A-B and the can electrode 112 can be represented by the sum of the tissue resistance of the resistor 113C with the corresponding one of the tissue resistances of the resistors 113A or 113D, respectively; and the impedance between the respective RV electrodes 110A-B and the can electrode 112 can be represented by the sum of the tissue resistance of the resistor 113C with the corresponding one of the tissue resistances of the resistors 113B or 113E, respectively.

In the example of FIG. 1, the electrodes on the leads can be individually coupled, such as by respective wires in such leads, back to respective terminals in the IMD electronics unit 104. For example, the RA tip electrode 108A can be connected to an RA tip terminal 114A in the IMD electronics unit 104; the RA ring electrode 108B can be connected to an RA ring terminal 114B in the IMD electronics unit 104; the RV tip electrode 110A can be connected to an RV tip terminal 116A in the IMD electronics unit 104; the RV ring electrode 110B can be connected to an RV ring terminal 116B in the IMD electronics unit 104; and the can electrode 112 can be connected (e.g., within the IMD electronics unit 104, rather than via a lead) to a can electrode terminal 118 in the electronics unit 104.

In an example, the IMD electronics unit 104 can include circuitry for generating an electrostimulation energy, storing the electrostimulation energy, and delivering the electrostimulation energy to the tissue of the subject, such as described in Lyden et al. U.S. patent application Ser. No. 12/328,603 entitled CONFIGURATION OF PACING OUTPUT CHANNELS, which was filed on Dec. 4, 2008, and which published on Jun. 11, 2009 as U.S. Patent Publication No. US-2009-0149905-A1, and which is assigned to Cardiac Pacemakers, Inc., and which is incorporated herein by reference in its entirety, including its description of pacing output channels. For example, a RA pacing electrostimulation voltage can be generated and stored on a first terminal of a RA pacing electrostimulation supply capacitor 120A, the other terminal of which can be connected to a ground reference voltage 122; a RV pacing voltage can be generated and stored on a first terminal of a RV pacing supply capacitor 120B, the other terminal of which can be connected to the ground reference voltage 122.

In an example, a switch can be closed to deliver an RA electrostimulation. For delivering a RA bipolar electrostimulation, this can include selectively connecting the RA pacing electrostimulation supply capacitor 120A to the RA ring terminal 114B, such as by closing the switch 124A during a pace ("P") electrostimulation time period; the return path can be from the RA tip terminal 114A through a switch 128A and a coupling capacitor 130A to the ground reference voltage 122. For delivering a RA unipolar electrostimulation, this can include selectively connecting the RA pacing electrostimulation supply capacitor 120A to the can terminal 112, such as by closing the switch 126A during an electrostimulation ("P") time period; the return path can be from the RA tip terminal 114A through the switch 128A and the coupling capacitor 130A to the ground reference voltage 122.

For delivering an RV bipolar electrostimulation, this can include selectively coupling the RV pacing supply capacitor 120B to the RV ring terminal 116B, such as by closing the switch 124B during a pace ("P") electrostimulation time period; the return path can be from the RV tip terminal 116A through a switch 128B and a coupling capacitor 130B to the ground reference voltage 122. For delivering a RV unipolar electrostimulation, this can include selectively connecting the RV pacing supply capacitor 120B to the can terminal 112, such as by closing the switch 126B during a pace ("P") electrostimulation time period; the return path can be from the RV tip terminal 116A through the switch 128B and the coupling capacitor 130B to the ground reference voltage 122.

In an example, a delivered electrostimulation can be followed by an opposite polarity recharge pulse, which can be charge-balanced with the electrostimulation pulse, but which need not have the same amplitude as the electrostimulation pulse (e.g., a recharge pulse of lower amplitude and longer duration than the electrostimulation pulse can be used, such as to provide charge balance). For delivering a RA bipolar recharge pulse, a switch 132A can be closed, such as to connect the RA ring terminal 114B to the ground reference voltage 122; the return path can be from the RA tip terminal 114A through the switch 128A and the coupling capacitor 130A to the ground reference voltage 122. For delivering a RA unipolar recharge pulse, a switch 132C can be closed, such as to connect the can terminal 112 to the ground reference voltage 122; the return path can be from the RA tip terminal 114A through the switch 128A and the coupling capacitor 130A to the ground reference voltage 122.

For delivering a RV bipolar recharge pulse, a switch 132B can be closed, such as to connect the RV ring terminal 116B to the ground reference voltage 122; the return path can be from the RV tip terminal 116A through the switch 128B and the coupling capacitor 130B to the ground reference voltage 122. For delivering a RV unipolar recharge pulse, a switch 132C can be closed, such as to connect the can terminal 112 to the ground reference voltage 122; the return path can be from the RV tip terminal 116A through the switch 128B and the coupling capacitor 130B to the ground reference voltage 122.

In the IMD electronics unit 104, certain components can be included on an integrated circuit (IC) chip, while other components can be located off-chip. In an example, off-chip components can include the capacitors 120A-B, 130A-B, and electromagnetic interference (EMI) filter capacitors 135A-D, which can be used to filter unwanted high-frequency noise, such as at the terminals 114A-B, 116A-B, and 118. In an example, the EMI filter capacitors 136A-D can each have a first terminal that can be connected to a respective one of the terminals 114A-B, 116A-B, and can each have a second terminal that can be connected to the terminal 118.

In an example, the switches 124A-B, 126A-B, 128A-B, and 132A-C can be located on the integrated circuit chip, which can input/output (I/O) pads that are electrically connected to the terminals 114A-B, 116A-B, and 118, which, in turn, can be connected to their respective electrodes via respective conductors. In a bulk CMOS n-well semiconductor processing example, on the IC chip, at the I/O pads or at on-chip switches that are respectively connected to the terminals 114A-B, 116A-B, and 118, parasitic IC substrate diodes 134A-E can exist. In such a n-well semiconductor processing example, the parasitic IC substrate diodes 134A-E can include respective cathodes connected at the IC I/O pads corresponding to the respective terminals 114A-B, 116A-B, and 118, and respective anodes commonly connected to the reference voltage to which the IC substrate is connected, such as the ground reference voltage 122. In such an n-well semiconductor processing example, parasitic n-well diodes 136A-E can also exist. In such an n-well semiconductor processing example, the parasitic IC n-well diodes 136A-E can include respective anodes at or connected to the IC I/O pads connected to the respective terminals 114A-B, 116A-B, and 118, and respective cathodes commonly connected to the reference voltage to which the IC n-well is connected, such as the VDD positive power supply reference voltage 138. In an example in which multiple positive power supply reference voltages are provided (e.g., as an illustrative example, a lower VDD=3.0V such as to supply electronic circuitry on the IC, and a higher VCC=12V such as to provide a higher voltage for providing electrostimulation pulses, or for powering a flyback DC-to-DC power converter circuit for generating an even larger defibrillation shock voltage) the diode cathodes can be commonly connected to the higher VCC positive power supply reference voltage, rather than to the lower VDD positive power supply reference voltage.

Figure 2:
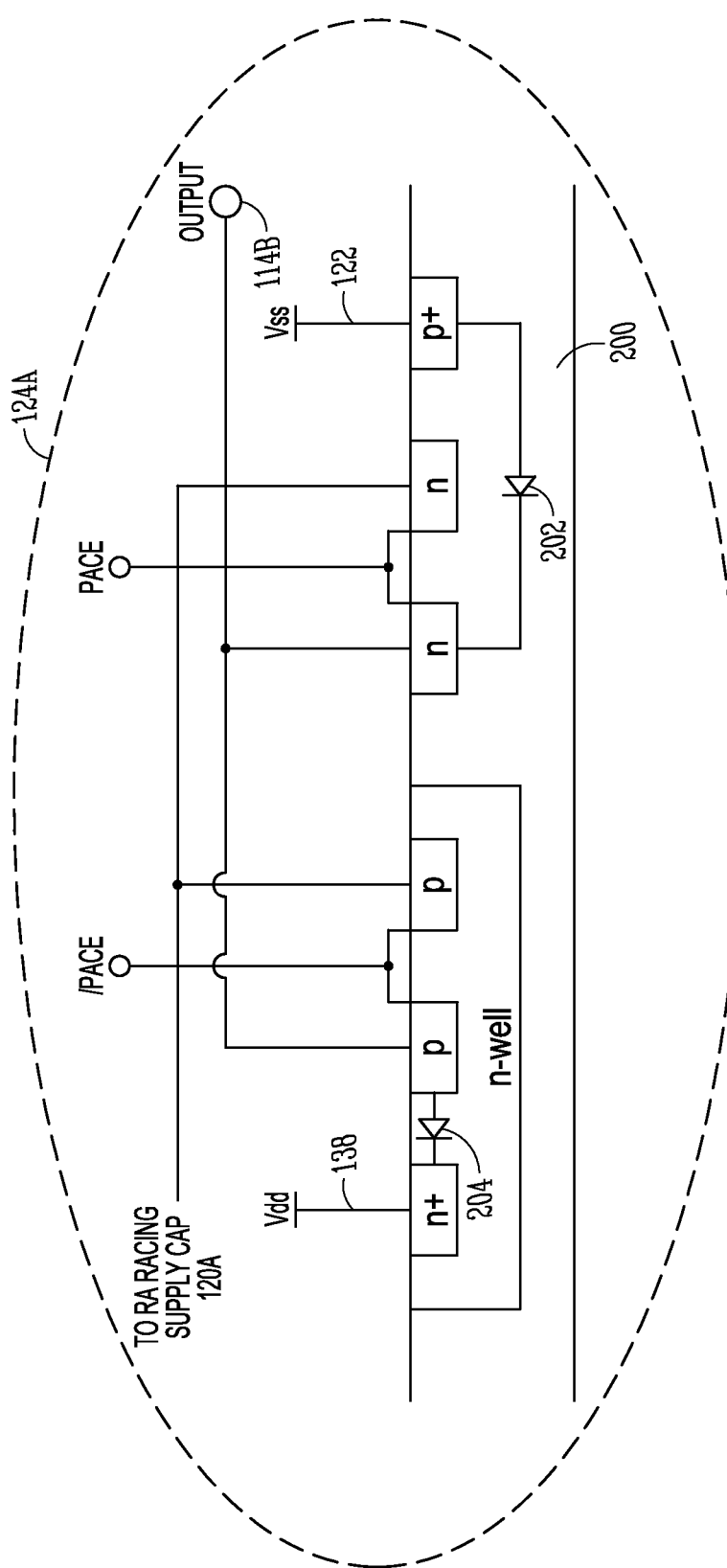
FIG. 2 shows a cross-sectional example of an n-well CMOS implementation of an electrical switch, providing an illustrative example of an IC including an IC parasitic substrate diode and an IC parasitic n-well diode.

FIG. 2 shows a cross-sectional example of an n-well CMOS implementation of switch 124A, providing an illustrative example of an IC 200 including an IC parasitic substrate diode 202 and an IC parasitic n-well diode 204. In an example, unintended current can flow through parasitic substrate or n-well diodes, such as when the output pad voltage at 114B rises above the most positive IC bias voltage (e.g., the VDD positive power supply reference voltage 138) or falls below the most negative IC bias voltage (e.g., the VSS ground reference voltage 122). Upon reviewing FIGS. 1-2, it can become apparent that an analogous situation can arise if the IC uses a p-well bulk CMOS semiconductor process, rather than the n-well bulk CMOS semiconductor process illustrated in the examples of FIGS. 1-2. Although FIG. 2 illustrates the particular example of switch 124A, similar circuit arrangements and considerations can apply to the other IC switches.

Figure 3:
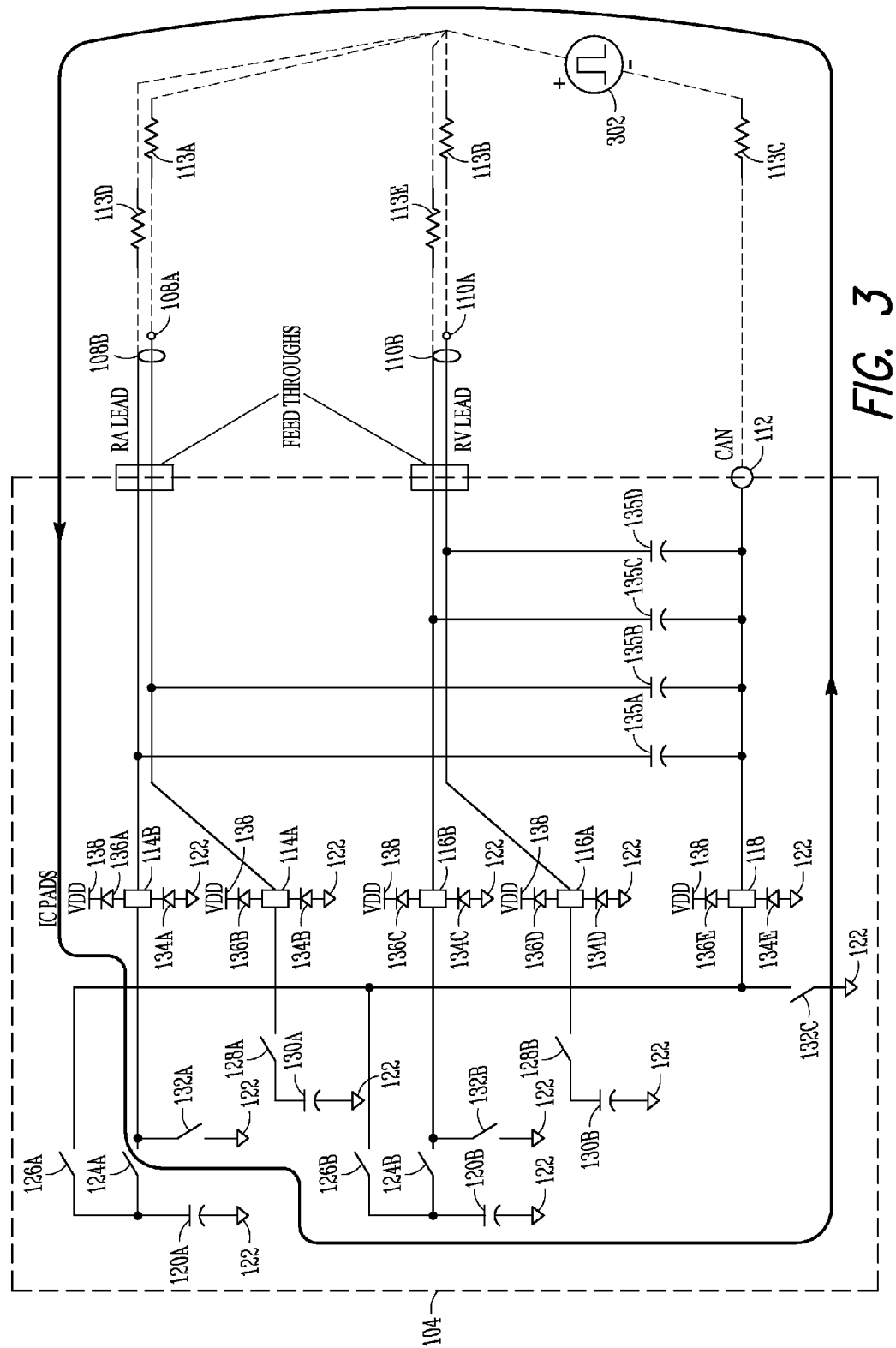
FIG. 3 shows an example illustrating how an EMI external voltage source can cause a voltage to develop, such as between the can electrode and one or more electrodes that are located at the distal end of an electrostimulation lead.

FIG. 3 shows an example illustrating how an EMI external voltage source 302 can cause a voltage to develop, such as between the can electrode 112 and one or more electrodes (e.g., 108A-B, 110A-B) that are located at the distal end of an electrostimulation lead 106. In an example, an electromagnetic field (EMF) can develop along a loop formed by the lead wires en route to their distal electrodes (e.g., 108A-B, 110A-B) and a return ionic conductive tissue path back to the can electrode 112. The EMI source 302 in the example of FIG. 3 can represent one or more of a plethora of possible external interference sources, such as electrocautery, an RF ablation catheter, or induced EMF due to MRI time-varying gradient. In the case of MRI gradient field induction across the leads 106A-B, the EMF voltage can develop along the leads 106A-B.

In an illustrative cardiac pacer example, there can be up to three leads implanted in the patient, each starting from the IMD electronics unit 104 (e.g., implanted at a subcutaneous pectoral location) and following a similar intravascular trajectory to the heart, with distal portions of the leads terminating in association with respective right atrial (RA), right ventricular (RV), and left ventricular (LV) chambers of the patient's heart. If each such pacing lead follows a similar trajectory, which is typically the case, then the MRI gradient field induced EMF generated between closely spaced electrodes at the distal end of the RA, RV, and LV leads will be very similar. This can result in small, perhaps negligible voltage between the distal end electrodes 108A-B, between 110A-B, or between 108A-B and 110A-B, in some cases. In other cases, it may be possible for a significant (e.g., exceeding a diode forward turn-on voltage of 0.7V) differential voltage to develop between (1) electrodes 108A-B and (2) electrodes 110A-B, such as where RA and RV leads are of differing lead length and excess lead length is coiled in the pocket in which the implantable device electronics unit 104 is implanted. Such a situation can arise not only with a pectorally or abdominally implanted cardiac rhythm management device, but also for other types of ambulatory or implantable medical devices. For example, lead length can be significantly longer in some neurostimulation devices, such as a lumbar spinal cord stimulator, for example, in which a left and right lead trajectory are not constrained by a common conduit as in the case of transvenous approach to the heart.

Moreover, in the example of FIG. 3, a significant large "common mode" voltage can develop between the distal end electrodes 108A-B, 110A-B and the can electrode 112. This common mode voltage can reach several volts. An upper value for the common mode voltage can be estimated by multiplying an estimated largest expected (e.g., mean+3 standard deviations) lead loop area (e.g., 377 cm$^2$, such as identified in a PC-69 cell phone interference example) by the gradient field (dB/dt) of the MRI scanner. For a gradient field (dB/dt) strength of 100 Teslas per second per axis, such as associated with the strongest commercially available 1.5 T and 3.0 T MRI scanners, the resulting upper value for the common mode voltage can be so estimated at about 3.77 Volts.

The IMD electronics unit 104 can include pacing or sensing circuitry that can be selectively coupled to the distal electrodes (e.g., 108A-B, 110A-B). Such circuitry may be subjected to such large common mode voltages. If not properly designed, the MRI-induced resulting common mode voltage may forward-bias semiconductor IC junctions, such as the substrate diode 202, the n-well diode 204, or other pn junctions on the IC. For example, this can occur when the external electrodes are driven by MRI-induced or other interference to a voltage that is above the VDD positive power supply reference voltage 138 or below the VSS ground reference voltage 122.

In an example, when the electrostimulation switches 124A-B or 126A-B, recharge switches 132A-C, and return switches 128A-B are off, the external gradient emf voltage source 302 does not generate charge or current flow through the substrate of the IC 200 because these circuit paths are blocked by the reverse-biased substrate diode 202 of the substrate diodes 134A-E. However, for example, in delivering a RA pace electrostimulation and recharge, during the RA recharge pulse (e.g., following a RA pace electrostimulation pulse), the RA recharge switch 132A is closed. The closed RA recharge switch 132A shunts the substrate diode 134A, which is connected to the RA ring electrode 108B being electrostimulated and recharged. The MRI-induced voltage source 302 can forward-bias the substrate diode of an electrode not being electrostimulated, such as for example the substrate diode 134E associated with the can electrode 112. This can cause the substrate diode 134E to turn on and conduct current, which can flow through the substrate 200, and through the RA recharge switch 132A, which can return current through the RA ring electrode 108 back to the MRI-induced voltage source 302. In this way, the MRI gradient-induced voltage source 302 can cause current to pass through the can electrode 112 or other electrodes that are intended to be "off"

The magnitude of the unintended substrate currents can depend upon the magnitude of the common mode voltage presented by the MRI-induced voltage source 302 and the exponential current-voltage transfer characteristic of the substrate diodes 202 of the substrate diodes 134A-E. In an example, the unintended substrate current can exceed the capture threshold for cardiac or neural stimulation. This can transform an intended bipolar electrostimulation or recharge into an unintended unipolar electrostimulation or recharge. In an example, the unintended substrate current can cause an unintended "recharge" of the electrodes intended to be electrostimulated. In a similar way, a pace electrostimulation or recharge in an intended chamber (e.g., RA) can be transformed into a pace electrostimulation or recharge of an unintended chamber (e.g., RV).

The consequence of an MRI gradient-induced voltage can be an unintended electrostimulation to a cardiac region that was not intended to be stimulated, which can be problematic for a patient. For example, in a dual-chamber (e.g., DOO) pacing mode, this can cause an unintended ventricular electrostimulation accompanying each delivered atrial electrostimulation, together with an intended ventricular electrostimulation with each intentionally-delivered ventricular electrostimulation. This can cause the heart to be electrostimulated twice as fast as intended by the programmed pacing rate of the pacer—once during the intended ventricular electrostimulation, and again, unintentionally, during the atrial electrostimulation that is accompanied by the unintended ventricular electrostimulation. In a similar way, the ventricular electrostimulation pulse may cause unintended current to flow via a parasitic substrate diode associated with an atrial distal electrode 108A-B (e.g., causing loss of atrioventricular synchrony) or via a parasitic substrate diode associated with the can electrode 112.

Figure 4:
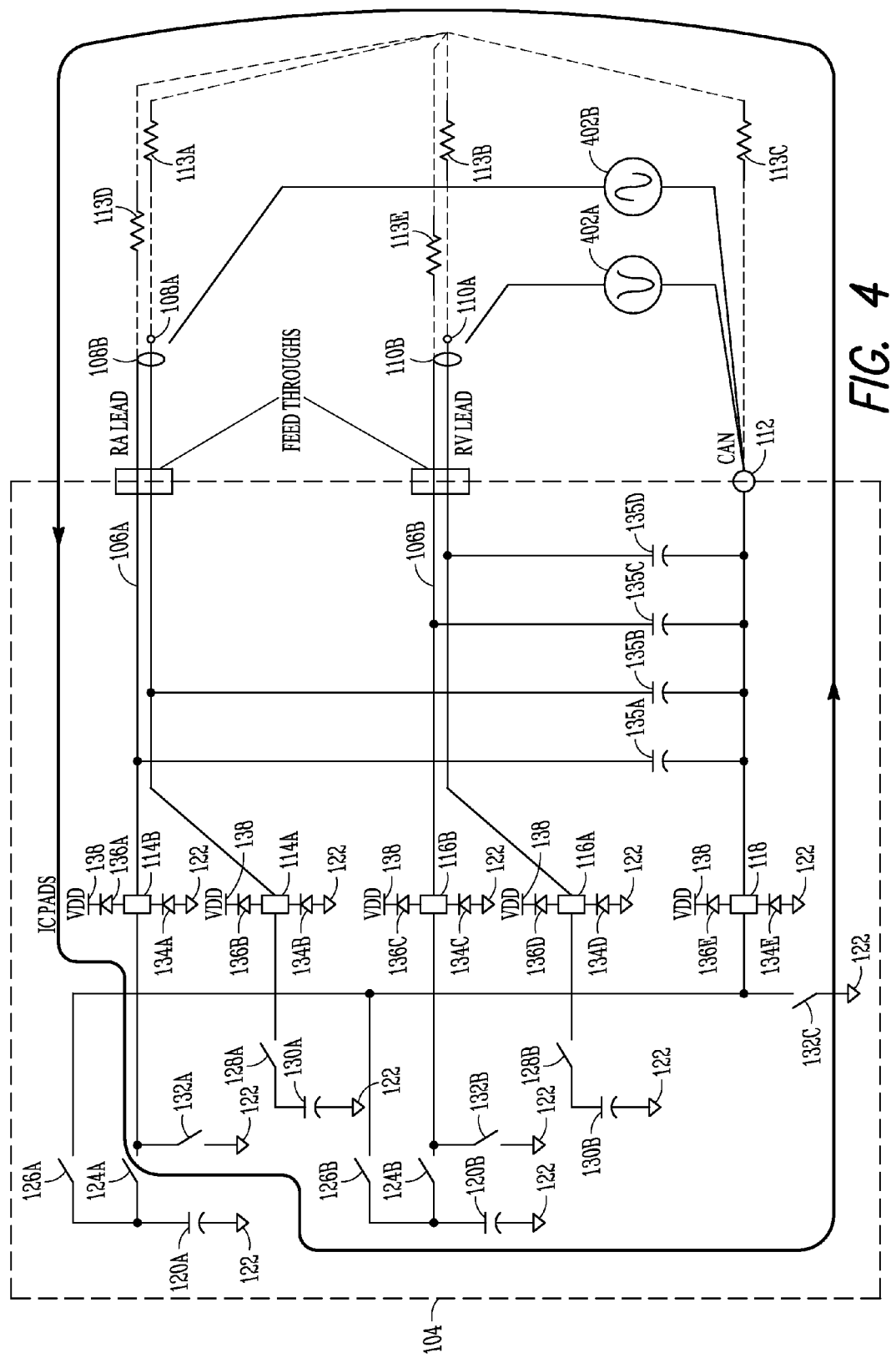
FIG. 4 shows an example of another potential MRI effect that can involve the parasitic substrate diodes: possible rectification of the MRI radiofrequency (RF) field.

FIG. 4 shows an example of another potential MRI effect that can involve the parasitic substrate diodes 202 (of the substrate diodes 134A-E) or corresponding well diodes 204 of FIG. 2: possible rectification of the MRI radiofrequency (RF) field. An MRI device can include a powerful pulsed RF field source (e.g., 15-30 kW), which can be used to process the patient's hydrogen atom nuclei spins during MRI scanning of the patient. During each RF pulse, an electric field (E-field) can form, such as tangentially along the leads 106A-B that are connected to the IMD electronics unit 104. This can produce RF currents in the conductors in the leads 106A-B. The resulting MRI RF-induced currents in the leads 106A-B can cause a voltage 402A-B to develop across an EMI capacitor 135A-D, such as shown in the example of FIG. 4. Variations in lead length, lead orientation or trajectory, and MRI RF-induced tangential E-field can generate differences in phase between the voltage 402A and the voltage 402B, such as illustrated in the example of FIG. 4.

Generally, the EMI filter capacitors 135A-D can shunt lead current to the conductive case, housing the IMD electronics unit 104, which is connected to the can electrode 112. This can help protect the electronic circuitry internal to the IMD electronics unit 104 from external interference. It is desirable that the EMI filter capacitors 135A-D should keep the voltage difference between the various lead electrodes (e.g., 108A-B and 110A-B) and the can electrode 112 negligibly small. However, the RF voltage appearing across the EMI capacitors 135A-D, which is a function of the impedance of the EMI filter capacitors 135A-D and the magnitude of the RF currents in the leads 106A-B can, in certain circumstances (e.g., in an MRI setting) become significant. Parasitic inductance along the connections to the EMI filter capacitors 135A-D and the can electrode 112 can also contribute to developing a voltage across the connections of the housing feedthroughs (e.g., extending through the conducting housing of the IMD electronics unit 104, helping provide electrical connections from respective external terminals connected to the leads to corresponding internal terminals connected to IC circuitry in the IMD electronics unit 104. This can expose the electronic circuits within the IMD electronics unit 104 to unintended activation of (and rectification by) substrate diodes, such as in a similar manner to that discussed above for the MRI gradient-induced voltages and resulting currents.

In the example of FIG. 4, for convenience and ease of understanding, the distributed RF antenna pickup of the lead can be simplified and represented as a lumped circuit element, e.g., such as by representing the situation using a voltage source of arbitrary phase at a distal end of the lead, such as can be associated with the patient's heart. In reality, the radiated electric field pick-up and propagation of current or voltage down the lead is a more complicated phenomenon that can be represented and solved more accurately, such as by using a computerized electromagnetic field solver. The RF voltage that can develop between the internal (e.g., within the housing of the IMD electronics unit 104) connections to a lead electrode and to the can electrode 112 can be characterized as the product of the RF current flowing through the proximal side of the patient lead and the input reactance of the EMI filter capacitor 135 to the can electrode 112. Generally, the proximal side (near the housing of the IMD electronics unit 104) RF lead current can depend more on the lead length, internal construction and its component geometry and its resulting distributed impedance than on the proximal end termination impedance over a wide range of capacitance values of the EMI capacitors 135. If the IMD 102 does not employ EMI filter capacitors 135, then the RF voltage that develops between the various lead connections of the IMD electronics unit 104 and the housing connection 118 or can electrode 112 can depend on the input impedance that the electronics within the IMD electronics unit 104 present to the patient lead system.

If MRI gradient-induced EMF or the MRI RF or other RF induced voltage exceed the forward turn-on voltage of the IC parasitic substrate or electrical switch diodes, then rectification may occur and unintended low frequency currents may flow, such as between a heart electrode and the can electrode 112, or potentially between distal heart or other patient electrodes. A possible effect of such an unwanted current, such as when the IMD 102 comprises a cardiac pacer, may include unintended cardiac electrostimulation.

Figure 5A:
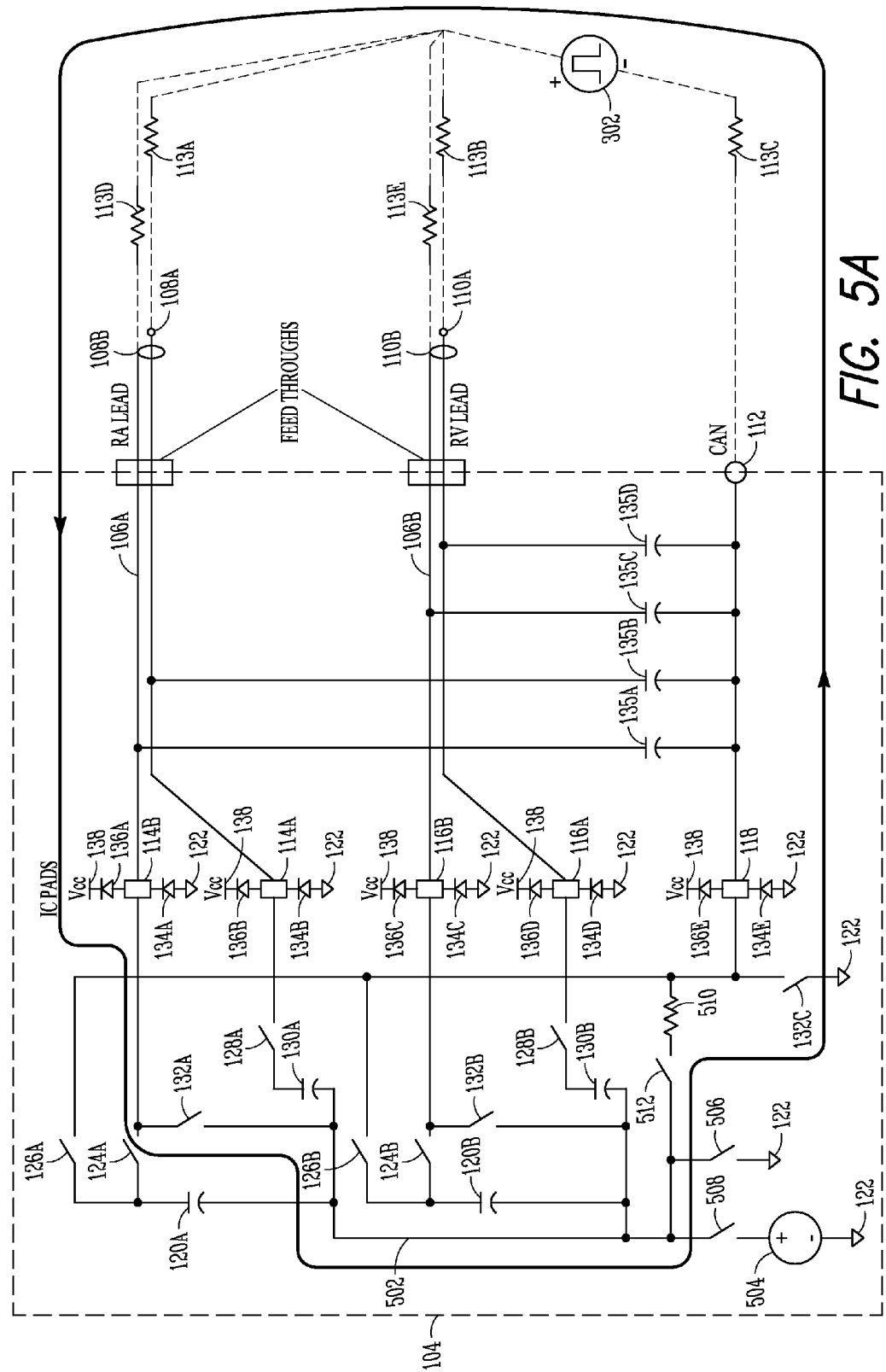
FIG. 5A shows an example of a solution that can help reduce or avoid such MRI gradient-induced and MRI RF-induced effects, such as rectification effects.

FIG. 5A shows an example of a solution that can help reduce or avoid such MRI gradient-induced and MRI RF-induced effects, such as rectification effects. In the example of FIG. 5A, a common-mode bias can be introduced, such as to avoid the undesired rectification of MRI or other external EMI sources by the electronic circuitry within the IMD electronics unit 104. Although FIG. 5A is illustrated, for conceptual clarity, with respect to the electrostimulation output circuitry of FIGS. 1-4 such as for pacing, such a common-mode bias technique can be applied to a neural stimulation circuit's current output circuitry or other IMD electronics of other types of IMDs.

In the example of FIG. 5A, the electrostimulation output capacitors 120A-B, the coupling capacitors 130A-B, and the recharge switches 132A-C can be connected to a dedicated "electrostimulation common mode" node 502. The electrostimulation common mode node 502 can be biased by a electrostimulation common mode bias voltage (VCM) 504, rather than to the VSS ground reference voltage 122, to which the integrated circuit substrate 200 is grounded. The electrostimulation common mode node 502 can be connected to a separate supply voltage 504. This can bias the electrostimulation common mode node 502 to a voltage that can be at a substantially higher voltage above the VSS ground reference voltage 122. This can help inhibit or avoid turn-on of the substrate diodes 202 of the substrate diodes 134A-E, even in the presence of MRI gradient-induced and MRI RF-induced voltages. In an example, the electrostimulation common mode bias voltage VCM 504 can include a fixed-value power supply or reference voltage generator. In an example, the electrostimulation common mode bias voltage VCM 504 can include a programmable value power supply or reference voltage generator, such as can be adjusted to accommodate the magnitude of the externally-impressed EMI voltage.

In an example, the electrostimulation output capacitors 120A-B can be charged, before electrostimulation delivery, while the electrostimulation common mode node 502 is connected, such as by closing a switch 506, to the VSS ground reference voltage 122, to which the IC substrate 200 is also connected. Then, during delivery of the electrostimulation or recharge, the switch 506 can be opened, and switch 508 can be closed, such as to selectively connect the electrostimulation common mode node 502 to the electrostimulation common mode bias voltage VCM 504. When the electrostimulation switches 124A-B or 126A-B, the recharge switches 132A-C, or the return switches 128A-B are closed, the substrate diode 202 of the substrate diodes 134A-E will not forward-bias when VCM exceeds the external EMI voltage potential less the turn-on voltage of the substrate diode 202. In an illustrative example, in which the EMI voltage is 3.77 volts, and the turn-on voltage of the substrate diode 202 is 0.5 volts, then if VCM exceeds 3.27 volts, the substrate diode 202 of the substrate diodes 134A-E will not turn on. As an additional note, a ground referencing resistor 510 (e.g., 100 KΩ) and series switch 512 can be included in the electrostimulation output circuitry. The switch 512 can be closed, when not delivering a electrostimulation or recharge, such as to selectively connect the can electrode 112 to the electrostimulation common mode node 502 through the resistor 510. This resistor 510 can help maintain a quiescent common-mode operating voltage at the can electrode 510, and similar resistors and switches can be used with respect to the other terminals of the IMD electronics unit 104, such as to help maintain their respective quiescent common mode operating voltages. Note, however, that in applications in which it is possible that the external EMF (e.g., a combined gradient and RF induced EMF) exceeds the VCM common mode stand-off voltage afforded by the CMOS process of the integrated circuit, it may be preferable not to close the switch 512 associated with the case ground referencing resistor 510 between intended output electrostimulation therapy pulses, such as to avoid even the small amount of rectified current through the series resistor 510 in the loop that it forms with the parasitic diode, as described above. Without such a resistor 510, the respective lead electrode voltages may "float" to any voltage between the negative power supply rail value (e.g., ground) and the positive power supply rail value (e.g., a VCC=12 V protection supply for the electrostimulation switches 124A-B or 126A-B and the recharge switches 132A-C). In an example, the resistor 510 can be selectively switched to the VSS ground reference voltage 122 during normal operation (e.g., by also closing the switch 506) and to the electrostimulation common mode node voltage 504 when the IMD electronics unit 104 is placed in an "MRI mode" of operation. In an example, the MRI mode of operation can be user-programmed, such as prior to MRI scanning of a patient. In an example, the MRI mode of operation can be automatically entered, such as in response to a sensor (e.g., Hall effect sensor, an inductor saturation detector, or the like) in the IMD electronics unit 104 detecting the presence of a magnetic field such as associated with an MRI scanner.

In an example, it can be preferable to generally always operate in the external EMI protection mode (e.g., the "MRI mode"). This can avoid having to switch back and forth between "normal mode" and "MRI mode". A consideration is that "normal mode" can, in some examples, generally provide a higher cardiac electrostimulation therapy pulse voltage output capability, because the common mode stand-off voltage of "MRI mode" can take up part of the operating voltage range between VDD and VSS. Another consideration is that the "MRI mode" battery demand can be higher than "normal mode" to achieve the same electrostimulation pulse output voltage pulse in an example in which the electrostimulation supply output needs to increase by the common mode voltage. Moreover, providing the common mode supply can in itself require additional energy to operate.

Figure 5B:
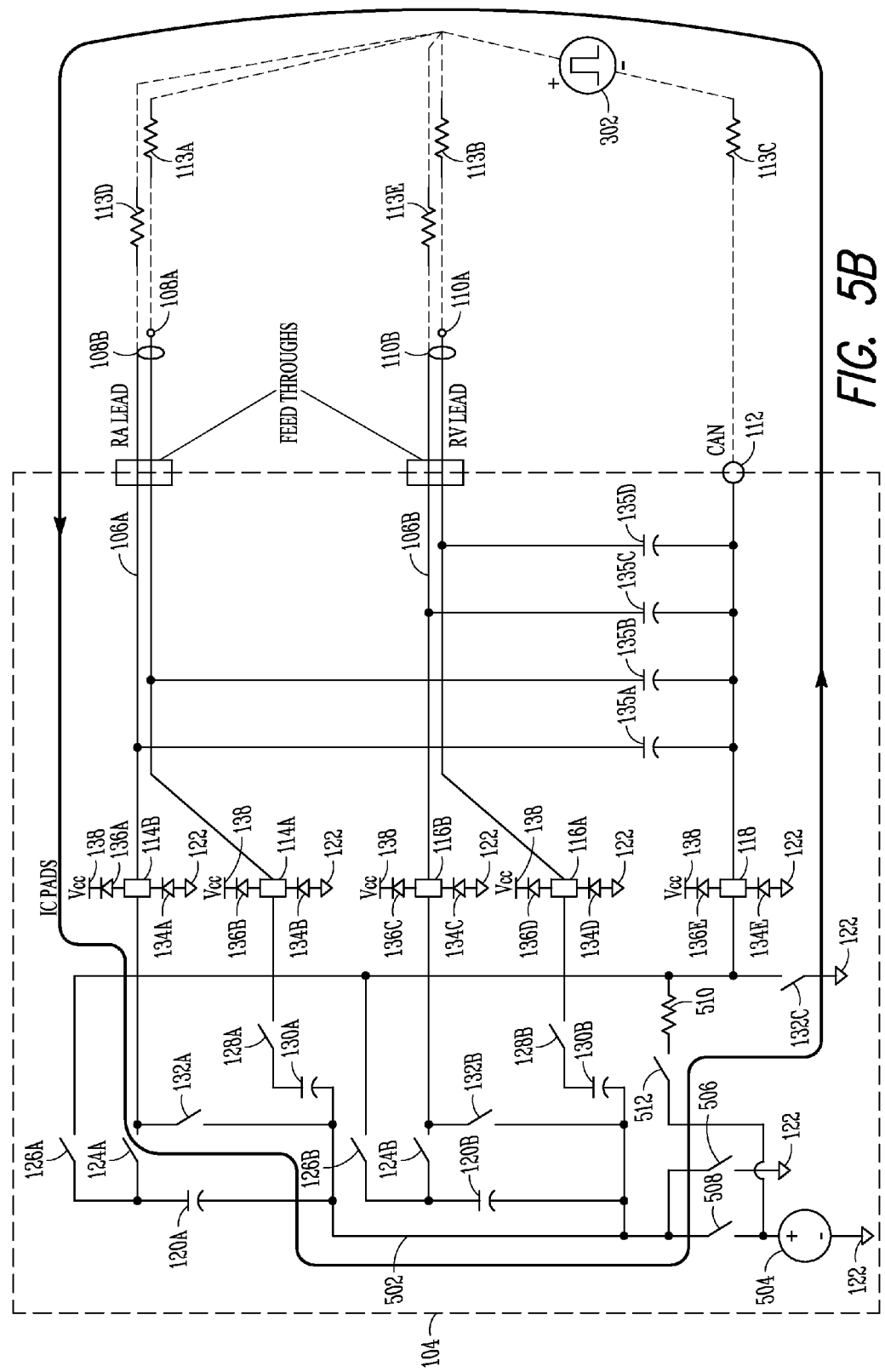
FIG. 5B shows an example, similar to that shown and described above with respect to FIG. 5B, but in which the series switch of the ground referencing resistor can be connected, such as directly, to an electrostimulation common mode node voltage.

FIG. 5B shows an example, similar to that shown and described above with respect to FIG. 5B, but in which the series switch 512 of the ground referencing resistor 510 can be unconnected from the electrostimulation common mode node 502, and instead connected, such as directly, to the electrostimulation common mode node voltage 504. In this example, when not delivering an electrostimulation (such as a pace) or sensing an ECG signal, the series switch 512 can be closed, such as to provide biasing that helps keep the substrate diodes 134A-E reverse-biased, and the series switch 512 can be opened otherwise.

Figure 6A:
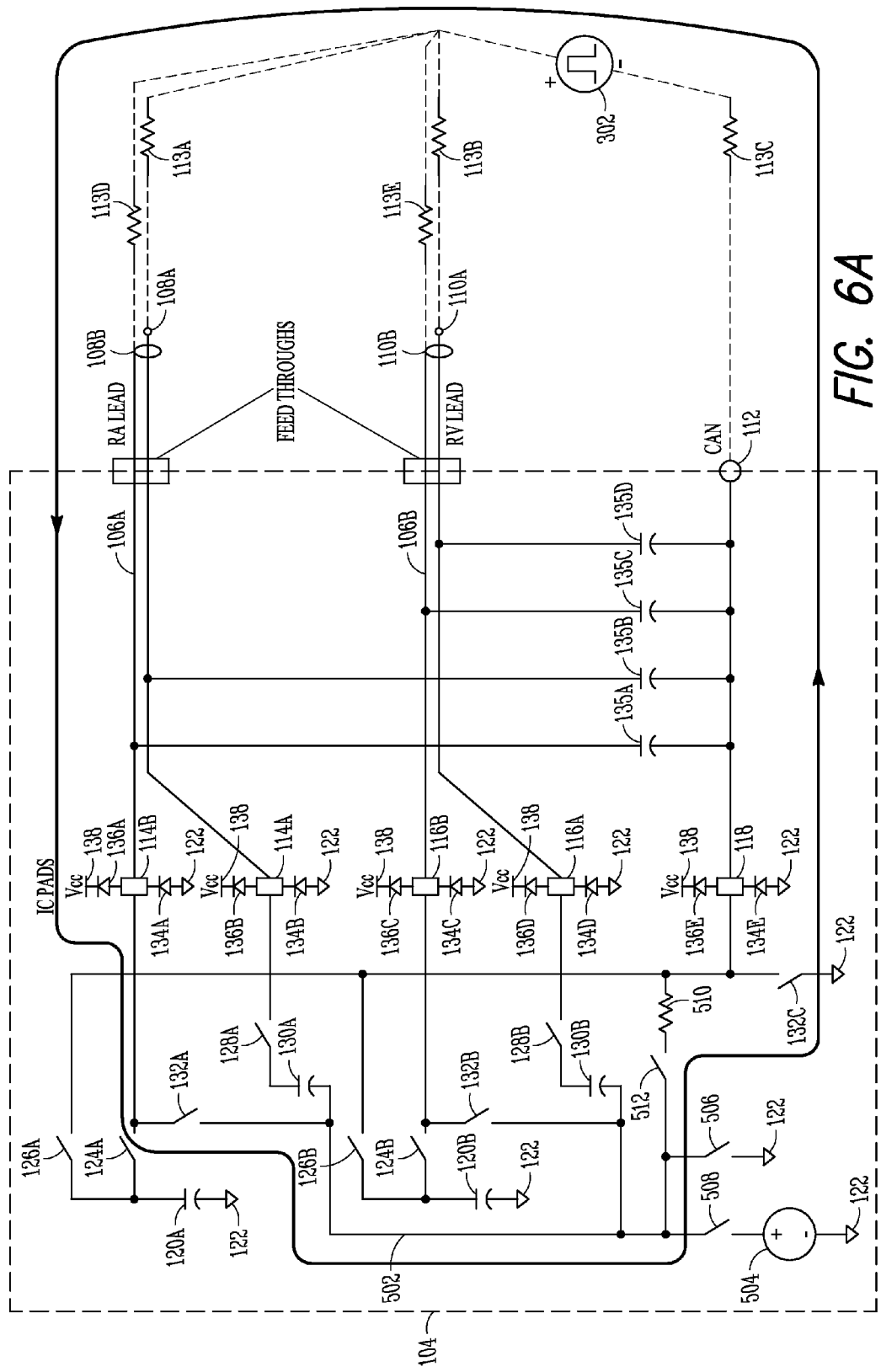
FIG. 6A shows another example of a solution that can help reduce or avoid such MRI gradient-induced and MRI RF-induced effects.

FIG. 6A shows an example of a solution that can help reduce or avoid such MRI gradient-induced and MRI RF-induced effects. In the example of FIG. 6A, a common-mode bias can be introduced, such as to avoid the undesired rectification of MRI or other external EMI sources by the electronic circuitry within the IMD electronics unit 104. Although FIG. 6A is illustrated, for conceptual clarity, with respect to the electrostimulation output circuitry of FIGS. 1-4, such a common-mode bias technique can be applied to a neural stimulation circuit's current output circuitry or other IMD electronics of other types of IMDs.

In the example of FIG. 6A, the electrostimulation output capacitors 120A-B and the coupling capacitors 130A-B can remain connected to the VSS ground reference voltage 122, instead of to the dedicated electrostimulation common mode node 502 of FIG. 5A. In the example of FIG. 6A, however, the recharge switches 132A-C can be connected to the dedicated electrostimulation common mode node 502. The electrostimulation common mode node 502 can be biased by an electrostimulation common mode bias voltage (VCM) 504, rather than to the VSS ground reference voltage 122, to which the integrated circuit substrate 200 is grounded. The electrostimulation common mode node 502 can be connected to a separate supply voltage 504. This can bias the electrostimulation common mode node 502 to a voltage that can be at a substantially higher voltage above the VSS ground reference voltage 122. This can help inhibit or avoid turn-on of the substrate diodes 202 of the substrate diodes 134A-E, even in the presence of MRI gradient-induced and MRI RF-induced voltages. In an example, the electrostimulation common mode bias voltage VCM 504 can include a fixed-value power supply or reference voltage generator. In an example, the electrostimulation common mode bias voltage VCM 504 can include a programmable value power supply or reference voltage generator, such as can be adjusted to accommodate the magnitude of the externally-impressed EMI voltage.

In the example of FIG. 6A, using the RA electrostimulation output channel as an illustrative example, an RA electrostimulation pulse can be issued from the RA pacing electrostimulation capacitor 120A by the RA pacing electrostimulation switch 124A. Following the RA electrostimulation, such as during an RA recharge pulse, the RA coupling capacitor 130A can be discharged to the electrostimulation common mode voltage VCM 504 at the electrostimulation common mode node 502. This can include closing the RA recharge switch 132A and closing the switch 508. In this example of the arrangement of FIG. 6A, the RA pacing electrostimulation capacitor 120A can be charged to a voltage exceeding the desired electrostimulation pulse amplitude value by an amount equal to the voltage provided by the electrostimulation common mode voltage VCM 504. This can compensate for the non-zero electrostimulation common mode voltage VCM 504 that is present across the RA coupling capacitor 130A during the recharge pulse. In this example of the arrangement of FIG. 6A, the leading edge amplitude of the electrostimulation voltage applied differentially across the electrostimulation electrodes (e.g., RA ring 108B and RA tip 108A) is the difference between the electrostimulation supply voltage setting (e.g., VCM+Vpace) and the voltage across the RA coupling capacitor 130A (e.g., VCM) after the recharge pulse is delivered.

In this example of the arrangement of FIG. 6A, during delivery of the electrostimulation or recharge, the switch 506 can be opened, and switch 508 can be closed, such as to selectively connect the electrostimulation common mode node 502 to the electrostimulation common mode bias voltage VCM 504. When the electrostimulation switches 124A-B or 126A-B, the recharge switches 132A-C, or the return switches 128A-B are closed, the substrate diode 202 of the substrate diodes 134A-E will not forward-bias when VCM exceeds the external EMI voltage potential less the turn-on voltage of the substrate diode 202. In an illustrative example, in which the EMI voltage is 3.77 volts, and the turn-on voltage of the substrate diode 202 is 0.5 volts, then if VCM exceeds 3.27 volts, the substrate diode 202 of the substrate diodes 134A-E will not turn on. This example can also include one or more ground referencing resistors, such as resistor 510, such as explained above.

In this example of the arrangement of FIG. 6A, the VCM voltage regulation can operate a bit differently than, for example, with respect to the arrangement of FIG. 5A. In the example of FIG. 5A, a regulated pacing voltage generator circuit (e.g., switched-capacitor, inductive switched-mode power supply, or other implementation) can be used to charge the respective pacing supply capacitors 120A-B to their desired voltages for delivering the electrostimulation. In the example of FIG. 5A, this generally involves charging and maintaining the electrostimulation supply capacitor 120A-B at the desired pacing voltage, such as programmed by a doctor, caregiver, or other user. In the example of FIG. 5A, during a electrostimulation pulse delivery, charge can be withdrawn from the electrostimulation supply capacitor 120A-B, and this withdrawn charge can be replenished after the electrostimulation pulse delivery. Therefore, in the example of FIG. 5A, the regulated pacing voltage generator circuit supplying charge to the particular pacing supply capacitor 120A-B can be designed to source current into the particular pacing supply capacitor 120A-B, and to maintain the voltage of the particular pacing supply capacitor 120A-B at the user-programmed setting. By contrast, in the example of FIG. 6A, during a recharge pulse delivery, the regulated pacing voltage generator circuit 504 supplying VCM to the electrostimulation common mode node 502 can be configured to shunt current from the electrostimulation common mode node 502 to the VSS ground reference voltage 122 during the recharge pulse, such as to prevent the voltage VCM at the electrostimulation common mode node 502 from increasing during the recharge.

Regulating VCM to a fixed common mode voltage throughout the recharge phase can help maintain a substantially constant capacitive circuit time constants, such as during electrostimulation and recharge phases, at $\tau$=Electrostimulated Impedance$\times ((C_{coupling} \cdot C_{electrostimulation\ supply})/(C_{coupling}+C_{electrostimulation\ supply}))$, where $C_{coupling}$ represents the capacitance value of the appropriate one of the coupling capacitors, such as one of coupling capacitors 130A-B, and $C_{electrostimulation\ supply}$ represents the capacitance value of the appropriate one of the electrostimulation supply capacitors, such as one of coupling capacitors 120A-B.

In an example, the steady-state tip coupling capacitor's potential after the recharge phase can differ between normal mode (e.g., 0V across the coupling capacitor) and MRI mode (e.g., VCM across the coupling capacitor). In an example, this difference can cause the delivered electrostimulation output voltage to be higher than its programmed setting immediately after transitioning into "MRI mode" from "normal" mode, such as until the blocking capacitor equilibrates to VCM potential over the next several electrostimulation/recharge cycles following the transition into MRI mode. Similarly, the delivered electrostimulation output voltage may be smaller than programmed immediately after transitioning back to "normal" mode from "MRI mode" until the coupling capacitor equilibrates back to 0V.

In an example, to avoid high transient electrostimulation pulse amplitudes that might cause, for example, undesirable diaphragmatic stimulation, or to avoid too low transient electrostimulation pulses that might cause intermittent loss of "capture," an algorithm that gradually increments pacing and common mode stand-off supply voltage to their final values can be employed. Also, a longer recharge interval can reduce the coupling capacitor equilibrate time.

In the examples of FIGS. 5A and 6A, to recap, a positive common mode voltage can be provided to portions of the electrostimulation circuitry, such as to keep parasitic substrate or well diodes from turning on and rectifying EMF energy induced by EMI sources such as electrocautery, RF ablation, or MRI scanning. In another example, the substrate 200 can be biased to a negative voltage with respect to a grounded (e.g., 0V) negative terminal of a battery powering the IMD electronics unit 104. In this example, the electrostimulation supply capacitors 120A-B, the recharge switches 132A-B, and the coupling capacitors 130A-B can be referenced to the grounded (e.g., 0V) negative terminal of the battery. In this example, the substrate diodes 134A-E can have their anodes referenced to the negative substrate voltage. The negative substrate voltage can be set to a value that is sufficiently negative with respect to the grounded (e.g., 0V) negative terminal of the battery to keep the diodes 134A-E from turning on and rectifying EMF energy induced by EMI sources such as electrocautery, RF ablation, or MRI scanning. This approach is similar to the approaches described above with respect to FIGS. 5A and 6A, but advantageously avoids higher-than-programmed pacing amplitudes, such as upon transition into MRI-mode, and therefore does not increase demand for energy provided by the battery. The negative bias voltage can be generated in a number of ways, such as by using a separate battery (there should be no appreciable current draw because it is used merely for providing a bias voltage, or by using an inductive voltage supply using a transformer with the positive side of the output winding tied to the grounded (e.g., 0V) voltage of the negative terminal of the battery, or using a capacitive charge pump.

Figure 6B:
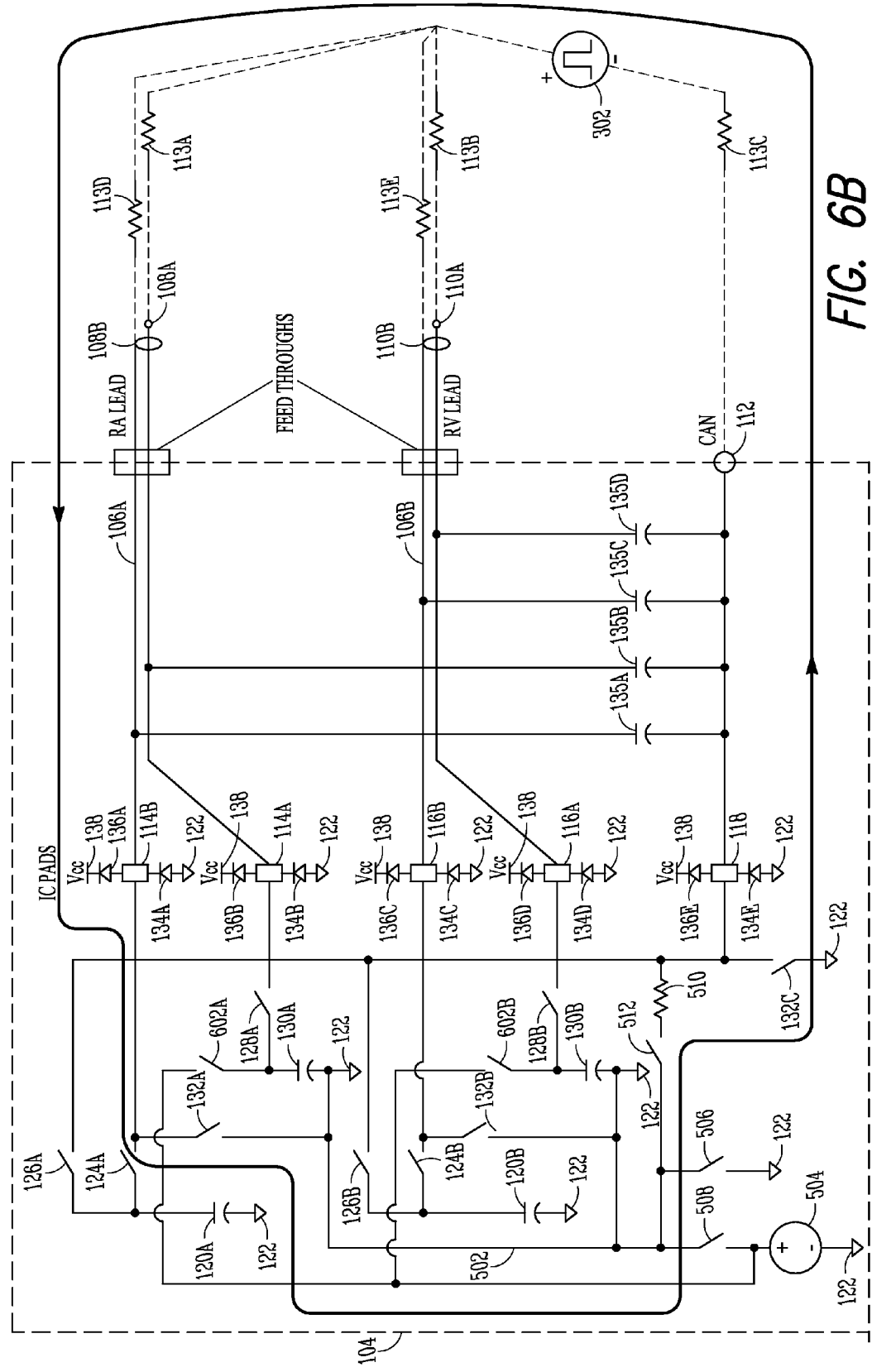
FIG. 6B shows an example, similar to that of FIG. 6A, but in which coupling capacitors can be referenced to a VSS ground reference voltage, and switchably pre-charged to a reference voltage, such as to an electrostimulation common mode voltage.

FIG. 6B shows an example, similar to that of FIG. 6A, but in which the capacitors 130A-B can respectively include a terminal that can be connected and referenced to the VSS ground reference voltage 122, and can respectively include another terminal that can be connected to the electrostimulation common mode voltage VCM 504, such as via respective switches 602A-B. In an example, the switches 602A-B can be used to pre-charge the capacitors 130A-B, such as to the voltage provided by the electrostimulation common mode voltage VCM 504.

In an example, an arrangement such as shown in FIG. 6B can also be used such as to help avoid a time delay associated with gradual transitioning of electrostimulation and common mode standoff voltages, such as during transitions to or from MRI mode. In an example, such a transition time delay can be avoided by:

1) actively pre-setting the voltage on the electrostimulation coupling capacitor to the MRI mode voltage bias after the last Normal mode electrostimulation pulse is delivered before MRI mode entry, and
2) actively pre-setting the voltage on the electrostimulation coupling capacitor to the Normal mode voltage level after the last MRI mode electrostimulation pulse is delivered before the transition back to Normal mode.

In an example, this transition can be accomplished after an electrostimulation recharge is completed, such as to provide charge balance on the cardiac electrodes, and before the first electrostimulation is delivered in the mode being entered. This can help the MRI mode transition be accomplished rapidly, such as between the delivery of the last electrostimulation pulse in a particular mode and the following electrostimulation pulse in the mode being transitioned to, with minimal effects on electrostimulation pulse amplitude following the transition.

Figure 7:
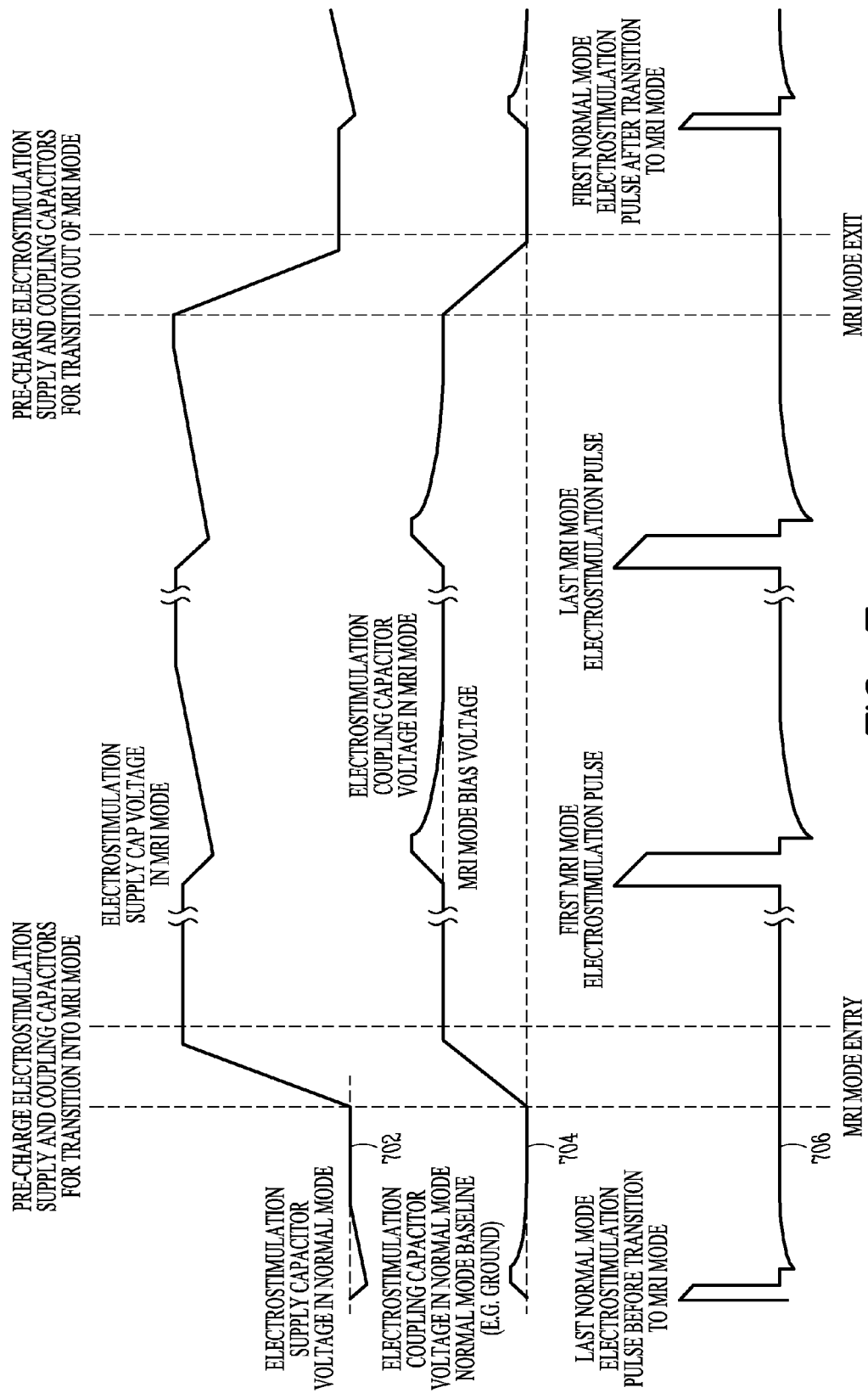
FIG. 7 is a voltage vs. time graph illustrating an example of waveforms during an example of such a transition process from Normal mode to MRI mode and back to Normal mode.

In an example, pre-charging of the coupling capacitors 130A-B can be accomplished using respective switches 602A-B in FIG. 6B. These switches 602A-B can be closed between electrostimulation pulses when transitioning between modes (e.g., from Normal mode to MRI mode, or vice-versa), such as to allow active management of voltage level on the coupling capacitors 130A-B. FIG. 7 is a voltage vs. time graph illustrating an example of waveforms during an example of such a transition process from Normal mode to MRI mode and back to Normal mode. FIG. 7 shows a waveform 706 of electrostimulation pulses over time before, during, and after MRI mode, including transitions therebetween, along with a corresponding waveform 702 of electrostimulation supply capacitor 120A-B voltage in Normal Mode and a corresponding waveform 704 of electrostimulation coupling capacitor 130A-B voltage in Normal mode. In an example, the following sequence can be used to accomplish the transition from Normal mode into MRI mode:
1) Allow recharge of the last electrostimulation pulse to be delivered in Normal Mode to complete. This can help preserve charge balance on the electrodes.
2) Close the switch 506 such as to provide a connection of the electrostimulation common node 502 to the Normal mode reference voltage, e.g., the VSS ground reference voltage 122, in this example.
3) Close the switch 510 to the lead and can electrodes to the Normal mode reference voltage, e.g., the VSS ground reference voltage 122, such as via the ground reference resistor 510 and the switch 506.
4) Close the switches 602A-B to connect the coupling capacitors 130A-B to the Normal Mode reference voltage, e.g., the VSS ground reference voltage 122, such as via the switch 506.
5) Open the switch 506.
6) Close the switch 508, such as to set the voltage level of the electrostimulation common node 502 to an MRI mode bias voltage, such as the reference voltage provided by the VCM voltage source 504.
7) Provide a delay sufficient to pre-charge the coupling capacitors 130A-B, such as to allow settling to a voltage level near that of the MRI mode bias voltage source provided by the VCM voltage source 504. In an example, this can be accomplished by allowing several time constants (e.g., greater than four time constants) of settling time. The settling time constant τ can be approximated, for example, as:

$$\tau = (C_{130A} + C_{130B}) * (RS_{504} + RSW_{508} + (RSW_{602A} * RSW_{602B})/(RSW_{602A} + RSW_{602B}))$$

where $C_{130A}$ and $C_{130B}$ are the capacitances of the coupling capacitors 130A, 130B respectively; $RSW_{508}$, $RSW_{602A}$ and $RSW_{602B}$ are the "on" resistances of the switches 508, 602A and 602B respectively; and $RS_{504}$ is the effective source resistance of the MRI bias voltage source, such as the VCM voltage source 504. This approximation can be used when the coupling capacitors 130A-B have similar capacitances, e.g., +/−20%, and the switches 602A-B have similar "on" resistances e.g., +/−20%.
8) Open the switches 602A-B. This can help ready the coupling capacitors 130A-B for use as charge balancing elements, such as for atrial and ventricular electrodes, respectively, during MRI-mode pacing electrostimulation. The switch 508 can remain closed, such as to reference the electrostimulation common node 502 to the MRI mode bias voltage 504. The switch 512 can remain closed to reference the lead and can electrodes to the MRI mode bias voltage level, e.g., the VCM voltage source 504.

The transition from MRI mode to Normal mode can similarly be accomplished, such as by using the below sequence:
1) Allow recharge of the last electrostimulation pulse to be delivered in MRI Mode to complete. This can help preserve charge balance on the electrodes.
2) Close the switch 508, such as to provide a connection of the electrostimulation common node 502 to the MRI mode bias voltage source, such as the VCM voltage source 504.
3) Close the switch 510, such as to reference the lead and can electrodes to the MRI mode bias voltage source, e.g., the VCM voltage source 504, such as via the resistor 510 and the switch 508.
4) Close the switches 602A-B, such as to connect the coupling capacitors 130A-B to the MRI mode bias voltage, e.g., the VCM voltage source 503, such as via the switch 506.
5) Open the switch 508.
6) Close the switch 506, such as to set the voltage level of the electrostimulation common node 502 to the Normal mode reference voltage level, e.g., the VSS ground reference voltage 122. Provide a delay sufficient to pre-charge the coupling capacitors 130A-B, such as to permit settling to a voltage level that is near that of the MRI mode bias voltage source, e.g., the VCM voltage source 504. This can be accomplished by allowing several time constants (e.g., greater than 4) of settling time for circuit elements, such as including the coupling capacitors 130A-B, and "on" resistances for the switches 602A-B and 506.
7) Open the switches 602A-B. This can help ready the coupling capacitors 130A-B, such as for use as charge balancing elements for atrial and ventricular electrodes respectively during Normal mode pacing. The switch 506 can remain closed, such as to reference the electrostimulation common node 502 to the Normal mode reference level. The switch 512 can remain closed such as to reference the lead or can electrodes to the normal mode reference level, e.g., the VSS ground reference voltage 122.

Additional Notes

The above detailed description includes references to the accompanying drawings, which form a part of the detailed description. The drawings show, by way of illustration, specific embodiments in which the invention can be practiced. These embodiments are also referred to herein as "examples."

Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile tangible computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The invention claimed is:

1. An apparatus comprising:
   an implantable medical device, comprising:
   an electrical energy delivery circuit, comprising:
   an integrated circuit including energy output circuitry, wherein the energy output eludes:
   a switch having an input terminal, an output, terminal, and a gate terminal, wherein the output terminal of the switch is electrically coupled to an output pad of the integrated circuit; and
   a common mode circuit node referenced to a reference voltage that is set at a specified value that is configured to provide a common mode bias to avoid turn-on of a parasitic well diode associated with the switch during at least:
   a magnetic resonance imaging (MRI) scanning, of a subject in which the implantable medical device is implanted, in an MRI scanner.

2. The apparatus of claim 1, in which the common mode circuit node is referenced to a reference voltage that is set at a specified value that avoids turn-on of the parasitic well diode associated with the switch during at least a magnetic resonance imaging (MRI) scanning, of a subject in which the implantable medical device is implanted, in an MRI seamier.

3. The apparatus of claim 1, wherein the common mode circuit node is referenced to a first reference voltage during a first mode of operation of the implantable medical device and referenced to a second reference voltage during a second mode of operation, and comprising:
   a controller circuit, configured to selectively connect the energy output circuitry to the first reference voltage during the first mode of operation, and to the second reference voltage during the second mode of operation, wherein the second mode of operation is configured to inhibit turn-on of the parasitic well diode associated with the switch in the presence of noise interference.

4. The apparatus of claim 3, wherein the switch is a recharge switch that is closed during a recharge pulse delivered in response to completion of delivery of an electrostimulation pulse, wherein the recharge switch is referenced to the first reference voltage during a first mode of operation of the implantable medical device and referenced to a second reference voltage during a second mode of operation.

5. The apparatus of claim 3, wherein the switch is an electrostimulation switch that is closed during delivery of an electrostimulation pulse, wherein the electrostimulation switch is referenced to the first reference voltage during a first mode of operation of the implantable medical device and referenced to a second reference voltage during a second mode of operation.

6. The apparatus of claim 3, wherein the switch is a return switch that is closed during delivery of either an electrostimulation pulse or a recharge pulse, wherein the return switch is referenced to the first reference voltage during a first mode of operation of the implantable medical device and referenced to a second reference voltage during a second mode of operation.

7. The apparatus of claim 3, wherein the energy output circuitry comprises an electrostimulation supply capacitor including a first terminal electrically coupled to an electrostimulation switch and a second terminal electrically coupled to the common mode circuit node, wherein the electrostimulation supply capacitor is referenced to the first reference voltage during a first mode of operation of the implantable medical device and referenced to a second reference voltage during a second mode of operation.

8. The apparatus of claim 3, wherein the energy output circuitry comprises a coupling capacitor including a first terminal electrically coupled to a return switch and a second terminal electrically coupled to the common mode circuit node, wherein the coupling capacitor is referenced to the first reference voltage during a first mode of operation of the implantable medical device and referenced to a second reference voltage during a second mode of operation.

9. The apparatus of claim 3, comprising a housing having an conductive portion and a can electrode located on the conductive portion, wherein the integrated circuit includes a resistor having a first terminal electrically coupled to the can electrode and selectively electrically coupled to the common mode circuit node during the MRI scanning.

10. The apparatus of claim 1, wherein the second reference voltage is set at a specified value that avoids turn-on of the diode during a magnetic resonance imaging (MRI) scanning in an MRI scanner of at least 1.5 Tesla.

11. The apparatus of claim 10, wherein the first reference voltage is set to a more negative voltage than the second reference voltage.

12. The apparatus of claim 11, wherein the first reference voltage is set to a negative battery terminal voltage.

13. An apparatus comprising:
an implantable medical device, comprising:
an electrical energy delivery circuit, comprising:
an integrated circuit including energy output circuitry, wherein the energy output circuitry includes:
an electrostimulation supply capacitor, configured to store an electrostimulation voltage to be delivered to a subject;
an electrostimulation switch, configured to selectively conduct current from the electrostimulation supply capacitor to be provided to the subject;
a coupling capacitor, configured to be located in the electrostimulation current path during an electrostimulation pulse, and configured to be discharged during a recharge pulse;
a recharge switch, configured to selectively discharge the coupling capacitor during the recharge pulse, wherein the recharge switch is located on the integrated circuit;
a common mode circuit node that is referenced to a first reference voltage during a first mode of operation of the implantable medical device and referenced to a second reference voltage during a second mode of operation, wherein the second reference voltage is set at a specified value to provide a common mode bias that avoids turn-on of parasitic well diodes associated with the electrostimulation switch and the recharge switch during a magnetic resonance imaging (MRI) scanning in an MRI scanner; and
a controller circuit, configured to selectively connect the common mode circuit node to the first reference voltage during the first mode of operation, and to the second reference voltage during the second mode of operation, wherein the second mode of operation is configured to provide increased noise-immunity to the implantable medical device by inhibiting turn-on of the parasitic well diodes in the presence of noise interference.

14. The apparatus of claim 13, wherein the controller circuit is configured to selectively connect the recharge switch to the second reference voltage during the second mode of operation.

15. The apparatus of claim 14, wherein the controller circuit is configured to additionally connect the electrostimulation supply capacitor to the second reference voltage during the second mode of operation.

16. A method comprising:
providing an implantable medical device comprising a first mode, configured for operation in an environment that does not include magnetic resonance imaging (MRI) scanning-of a subject in which the implantable medical device is implanted, and comprising a second mode configured for operation in an environment that does include at least magnetic resonance imaging (MRI) scanning of a subject in which the implantable medical device is implanted; and
referencing a common mode circuit node of energy output circuitry of the implantable medical device to a first reference voltage during the first mode and to a second reference voltage during the second mode to provide a common mode bias during the second mode.

17. The method of claim 16, wherein the referencing comprises referencing the energy output circuitry to a second reference voltage that is set to avoid turn-on of an integrated circuit parasitic well diode in the implantable medical device during at least:
a magnetic resonance imaging (MRI) scanning, of a subject in which the implantable medical device is implanted, in an MRI scanner.

18. The method of claim 17, wherein the referencing comprises referencing the energy output circuitry to a second reference voltage that is set to avoid turn-on of the integrated circuit parasitic well diode in the implantable medical device during a magnetic resonance imaging (MRI) scanning, of a subject in which the implantable medical device is implanted, in an MRI scanner.

19. The method of claim 18, wherein the referencing comprises referencing an electrostimulation recharge switch to the first reference voltage during the first mode and to the second reference voltage during the second mode.

20. The method of claim 19, wherein the referencing comprises referencing an electrostimulation supply capacitor to the first reference voltage during the first mode and to the second reference voltage during the second mode.

* * * * *